(12) United States Patent
Paulos et al.

(10) Patent No.: US 6,517,579 B1
(45) Date of Patent: Feb. 11, 2003

(54) METHOD AND APPARATUS FOR SECURING A SOFT TISSUE GRAFT TO BONE DURING AN ACL RECONSTRUCTION

(76) Inventors: Lonnie E. Paulos, 1369 Military Way, Salt Lake City, UT (US) 84103; Benjamin J. Ellis, 415 Crestview Dr., Park City, UT (US) 84098

( * ) Notice: Subject to any disclaimer, the term of this patent is extended or adjusted under 35 U.S.C. 154(b) by 0 days.

(21) Appl. No.: 09/655,703

(22) Filed: Sep. 6, 2000

(51) Int. Cl.⁷ .................................................. A61F 2/08
(52) U.S. Cl. ........................ 623/13.14; 606/73; 606/232
(58) Field of Search ........................ 623/13.14; 606/60, 606/72, 73, 232

(56) References Cited

U.S. PATENT DOCUMENTS

| | | | |
|---|---|---|---|
| 4,708,132 A | 11/1987 | Silvestrini | 128/92 |
| 4,927,421 A | 5/1990 | Goble et al. | 606/73 |
| 4,988,351 A | 1/1991 | Paulos et al. | 606/72 |
| 4,997,433 A | 3/1991 | Goble et al. | 606/64 |
| 5,151,104 A | 9/1992 | Kenna | 606/73 |
| 5,152,790 A | 10/1992 | Rosenberg et al. | 623/13 |
| 5,268,001 A | 12/1993 | Nicholson et al. | 606/72 |
| 5,314,429 A | 5/1994 | Goble | 606/96 |
| 5,385,567 A | 1/1995 | Goble | 606/96 |
| RE34,871 E | 3/1995 | McGuire et al. | 606/73 |
| 5,397,356 A | 3/1995 | Goble et al. | 606/73 |
| 5,417,692 A | 5/1995 | Goble et al. | 606/73 |
| 5,431,651 A | 7/1995 | Goble | 606/73 |
| 5,522,843 A | 6/1996 | Zang | 606/232 |
| 5,562,671 A | 10/1996 | Goble et al. | 606/73 |
| 5,584,835 A | 12/1996 | Greenfield | 606/73 |
| 5,630,824 A | 5/1997 | Hart | 606/139 |
| 5,649,940 A | 7/1997 | Hart et al. | 606/148 |
| 5,688,284 A | 11/1997 | Chervitz et al. | 606/96 |
| 5,690,655 A | 11/1997 | Hart et al. | 606/148 |
| 5,702,397 A | 12/1997 | Goble et al. | 606/72 |
| 5,713,897 A | 2/1998 | Goble et al. | 606/53 |
| 5,718,706 A | 2/1998 | Roger | 606/73 |
| 5,720,753 A | 2/1998 | Sander et al. | 606/104 |
| 5,720,765 A | 2/1998 | Thal | 606/232 |
| 5,720,766 A | 2/1998 | Zang et al. | 606/232 |
| 5,782,835 A | 7/1998 | Hart et al. | 606/79 |
| 5,824,011 A | 10/1998 | Stone et al. | 606/232 |
| 5,840,078 A | 11/1998 | Yerys | 606/151 |
| 5,849,004 A | 12/1998 | Bramlet | 606/232 |
| 5,871,504 A | 2/1999 | Eaton et al. | 606/232 |
| 5,895,425 A | 4/1999 | Grafton et al. | 623/16 |
| 5,899,921 A | 5/1999 | Caspari et al. | 606/232 |
| 5,902,321 A | 5/1999 | Caspari et al. | 606/232 |
| 5,904,685 A | 5/1999 | Walawalkar | 606/73 |
| 5,931,840 A | 8/1999 | Goble et al. | 606/73 |
| 5,961,520 A | 10/1999 | Beck, Jr. et al. | 606/72 |
| 5,961,521 A | 10/1999 | Roger | 606/73 |
| 5,964,764 A | 10/1999 | West, Jr. et al. | 606/72 |
| 5,968,045 A | 10/1999 | Frazier | 606/73 |
| 5,984,927 A | 11/1999 | Wenstrom, Jr. et al. | 606/72 |
| 6,336,940 B1 * | 1/2002 | Graf et al. | 128/898 |
| 6,355,066 B1 * | 3/2002 | Kim | 606/232 |

* cited by examiner

*Primary Examiner*—Paul B. Prebilic
*Assistant Examiner*—William H. Matthews (Howie)
(74) *Attorney, Agent, or Firm*—Kirton & McConkie; Dale E. Hulse; Berne S. Broadbent

(57) ABSTRACT

An anchoring apparatus and method of use are disclosed that secure a tendon or ligament within an interior opening of a bone structure is disclosed. The apparatus comprises a securing device, a retention device, and an anchoring device. The securing device has an elongated body with an outer surface and an inner surface wherein the tendon or ligament fits between the interior of the open bone structure and the outer surface of the securing device. The retention device has an elongated body and a retention head, wherein the retention device securely fits within the interior surface of the securing device. The anchoring or holding device connects to the retention head of the retention device and extends outside the interior opening of the bone structure to engage the outer surface of the bone structure to hold the retention device and securing device in a fixed position inside the bone structure.

10 Claims, 4 Drawing Sheets

METHOD AND APPARATUS FOR SECURING A SOFT TISSUE GRAFT TO BONE DURING AN ACL RECONSTRUCTION

BACKGROUND OF THE INVENTION

This invention relates to orthopedic surgical procedures and, more particularly, to surgical devices involved in replacing, reconstructing or securing synthetic or biological connective tissue to interior or exterior bone surfaces, or both. Further still, the present invention relates to attaching and maintaining a replacement anterior or posterior cruciate ligament (ACL or PCL) against a bone with an anchor support being placed upon an exterior surface of the bone.

The knee joint is one of the strongest joints in the body because of the powerful ligaments which bind the femur and tibia together. Although the knee is vulnerable to injury as a result of the incongruence and proximity of its articular surfaces, the knee joint provides impressive stability due to the arrangement and interacting strength of its ligaments, muscles and tendons.

To a layman, the operation of the human knee resembles the actions of a hinge joint. In reality, however, the knee joint provides complicated mechanical movements and maneuverability far more complex than a simple hinge mechanism in regards to the rotation and gliding motions that may occur at the joint. In addition, the motions of flexing and extending the knee (and, in certain positions, the slight rotation inward and outward of the knee), require a very detailed structural configuration to facilitate the associated, refined mechanical movements of the knee joint.

Structurally, the knee joint comprises two discs of protective cartilage called menisci, which partially cover the surfaces of the femur and the tibia. The menisci operate to reduce the friction and impact loading between the femur and the tibia during movement of the knee. The knee is also partly surrounded by a fibrous capsule lined with a synovial membrane, which secrets a lubricating fluid. Strong ligaments on each side of the knee joint provide support to the joint and limit the side-to-side motion and joint opening of the knee. Fluid filled sacs called bursas are located above and below the patella (kneecap) and behind the knee providing a means of cushioning the kneecap upon impact and helping with joint lubrication. Moreover, the quadriceps muscles run along the front of the thigh to straighten the knee, while the hamstring muscles run along the back of the thigh to bend the knee.

Two intra-articular ligaments of considerable strength, situated in the middle of the joint, are known as the cruciate ligaments. These ligaments are referred to as "cruciate ligaments" because they cross each other somewhat like the lines of the letter "X". The anterior and posterior cruciate ligaments receive their names in respect to the positioning of their attachment to the tibia. The primary function of the anterior cruciate ligament (ACL) is to provide a means for limiting hyperextension of the knee and preventing the backward sliding of the femur on the tibia plateau. The ACL also assists in limiting any medial rotation of the knee joint when the foot is solidly on the ground and the leg fixed in position. Conversely, the posterior cruciate ligament (PCL) primarily provides a means for preventing hyperflexion of the knee and preventing the femur from sliding forward on the superior tibial surface when the knee is flexed.

Although the structure of the knee provides one of the strongest joints of the body, the knee is usually one of the most frequently injured joints. Athletes and persons who perform tasks requiring a great deal of body rotation are the most susceptible to serious ligament stressing and tearing at the knee joint. Consequently, the growing number of ligament injuries has given rise to considerable innovative activity within the area of orthopedic medicine in an effort to create surgical procedures and devices for replacing and reconstructing torn or dislocated ligaments.

Typically the surgical procedures for ligament replacement and reconstruction involve tissues being grafted from one part of the body (autograft) to the original attachment sites of a torn or dislocated ligament. Once the ligament graft has been transplanted, it is then attached to the natural fixation sites of damaged ligament. For example, the replacement of the ACL may involve transplanting a portion of the patellar tendon to the attachment sites of the original ACL to assist in the reconstruction of the ACL in the knee joint.

The expectations of prior art orthopedic procedures typically relate to reconstructing or replacing natural ligaments so as to enable the recipient to return to his or her full range of activity in as short a period of time as possible. To that end, medical researchers have attempted to duplicate the relative parameters of strength, flexibility, and recovery found in natural ligaments of the body. Unfortunately, many of the prior art methods of reconstructing and replacing damaged ligaments have generally proven inadequate for immediately restoring full strength and stability to the involved joint. Furthermore, there has long been a problem of effectively fastening a ligament to a bone surface for the duration of a ligament's healing process, which process involves the ligament graft growing to an adjoining bone mass to restore mobility to the injured joint of an orthopedic patient.

Early ligament replacement procedures traditionally comprised extensive incisions and openings in the knee to attach a replacement ligament to bone surfaces at the fixation sites of the natural ligament. The ends of a grafted ligament were typically secured to exterior bone surfaces by driving stainless steel staples through or across the ligament and into the adjacent bone mass. The legs of the staples are generally adapted for piercing and penetrating tissue and bone mass, while maintaining a ligament at a specified connection site. Other various types of tissue fastening devices, such as channel clamps, were also designed by those skilled in the art. The channel clamps normally differed from the above-mentioned staple arrangement in that the channel clamp fixation devices comprise a plurality of components that do not require clinching in the conventional manner, as when setting a staple into a bone surface.

The use of stainless steel staples, however, and other related fixation devices have a number of disadvantages. For example, piercing and puncturing of the ligament by the legs of the staples or other fixation devices may result in serious damage to the cross-fibers of the ligament or tissue. Such damage may cause weakening in the tensile strength of the ligament and result in tearing along the cross-fibers of the ligament under normal physical stress. When puncturing or tearing of cross-fibers occurs, the time required for the ligament to heal increases, which in turn results in a significant extension in the amount of time required to rehabilitate the knee joint before allowing the patient to return to normal daily activities.

To reduce or eliminate the disadvantages of cross-fiber damage exhibited by staples and other related fixation devices that puncture the body of the ligament, improvements in the types of surgical devices and techniques were developed by those skilled in the art. For example, one such technique involves drilling a hole through a bone to form a channel wherein an anchoring device may be inserted with a ligament graft attached thereto. Typically, the ligament is maintained at a fixation site in the bone channel by passing a suture through one end of the ligament graft and thereafter attaching the other end of the suture to an anchoring device positioned at the face of the opening of the channel in the bone mass. Unfortunately, problems occur when trying to secure the threads of the suture to the anchoring device when a physician is working in restricted or confined areas. As a result, combination drilling devices operably coupled to suture anchors were designed for dealing with ligament placement problems in areas of restricted maneuverability.

After a period of time, significant disadvantages emerged wherein a number of the ligament grafts retained in bone mass by the combination drilling/anchor devices began to rupture and tear at their fixation sites around the area where the ligament was in direct contact with the sharp outer edges of the opening of the channel formed in the bone. For example, as replacement ligaments tolerate the stress and strain associated with normal physical activity, the ligament generally begins to fatigue when wearing against the sharp outer edges of a bone channel opening. This form of fatigue typically causes significant damage to the ligament by tearing or cutting into ligament cross-fibers, thus, weakening the connection of the replacement ligament at its reattachment site. Consequently, after a period of time, cross-fiber fatigue, commonly known as "sun-dial" or "windshield wiper" wear, may further result in dislocating the replacement ligament from its original fixation site.

Because of the significant disadvantages associated with "sun-dial" wear or fatigue on replacement ligaments, improved surgical procedures were developed offering arthroscopic-assisted techniques typically including the formation of passages or tunnels through bone mass, wherein natural or synthetic ligaments may be inserted. After the ligament graft has been inserted into the bone tunnel, a ligament anchoring device is generally used to connect one end of a ligament to the exterior of the bone mass. The anchoring means generally requires that the replacement ligament end or ends be advanced beyond the bone tunnel, with each ligament end being bent and secured onto the exterior surface of the bone. Nevertheless, unfavorable disadvantages of ligament bending was observed by those skilled in the art as typically resulting in a force concentration at the location of the ligament bend generally causing the cross-fibers of the ligament to weaken, potentially subjecting the ligament to the possibility of further tearing or rupturing, as in the case of ligament sundial wear. Additionally, exterior devices can rub and cause pain, requiring removal about 10% of the time.

In response to the problems associated with maintaining a replacement ligament graft at a fixation site, additional devices and techniques were developed offering means whereby a ligament may be retained within a bone tunnel by an endosteal fixation device, such as, for example, an interference screw. The threads of the interference screw are typically bored into the bone tunnel for recessed engagement with the attached bone and one end of the ligament graft, while maintaining the ligament at a fixation site within the bone tunnel. Unfortunately, puncturing, piercing and possible tearing generally results to the cross-fibers of the ligament when the ligament is in direct engagement with the sharp threads of the interference screw. In addition, the interference screw typically requires a ligament replacement graft to be attached to its original bone.

During flexion or extension of the ligament, tension loads tend to act against the fixation site of the ligament generally causing strain on the ligament against its fixation site. Under such strain, the facing of the threads of the interference screw generally effect a pinching or piercing of the ligament which may cause tearing or dislocation of the replacement ligament under the stress associated with normal physical activities. Consequently, when a grafted ligament suffers cross-fiber damage due to puncturing, piercing or tearing, the healing period for the ligament dramatically increases, thereby in effect, increasing the rehabilitation time for the patient to recover.

One of the preferred methods employed by a number of skilled physicians when repairing torn or dislocated ligaments involves the harvesting of an autograft patella tendon bone block for incorporation into a femoral socket. Although the use of a patella tendon bone block provides a number of advantages, especially when dealing with fixation of the replacement ligament, the harvesting of a patella bone block typically results in extensive morbidity to the knee joint, requiring a considerable amount of time for the knee joint to heal, before a patient can resume any normal physical activity.

As illustrated by the foregoing summary, efforts are continuously being made to improve the graft types, surgical methods and devices used in replacing and reconstructing torn or dislocated ligaments so as to make the process more efficient and effective. Unfortunately, significant disadvantages remain with all the presently known devices and methods offered by the prior art.

SUMMARY OF THE INVENTION

According to the present invention, an anchoring apparatus that secures a tendon or ligament within an interior opening of a bone structure is disclosed. The apparatus comprises a securing device, a retention device, and an anchoring device. The securing device has an elongated body with an outer surface and an inner surface wherein the tendon or ligament fits between the interior of the open bone structure and the outer surface of the securing device. The retention device has an elongated body and a retention head, wherein the retention device securely fits within the interior surface of the securing device. The anchoring or holding device connects to the retention head of the retention device and extends outside the interior opening of the bone structure to engage the outer surface of the bone structure to hold the retention device and securing device in a fixed position inside the bone structure.

The retention head of the retention device has a generally round shape with a flat side surface. The holding device is a washer like structure that has at least one retention spike to engage the bone structure and the retention device fits through an opening of the washer and the retention head fits against the inner perimeter of the holding device. The retention head acts as a ball joint and the holding device pivotally connects in a joint configuration. In an alternative embodiment, the holding device pivotally connects to the retention head via a pivot pin. Both the securing device and the retention device have threads or ridges on their outer surface. Further, the holding device includes a plurality of apertures that retain means for securing the tendon or ligament to the anchoring apparatus.

In yet another alternative embodiment, the holding device has a first portion that extends beyond the span of the interior opening to engage the outer surface of the bone structure and a wedge section, which friction fits within the interior opening of the bone structure. In this embodiment, the holding or anchoring device has a taper shape.

A method is furthered disclosed for anchoring or securing a tendon or ligament to a bone structure. The method has the steps of preparing a bone tunnel through the bone structure, preparing a soft tissue graft to attach to the tendon or ligament, grafting the soft tissue graft to the tendon or ligament, inserting the soft tissue graft within the bone tunnel, inserting a securing device within the bone tunnel with the graft between the securing device and an interior surface of the bone tunnel, and inserting a retention device within the securing device such that an anchoring device connected to a head of the retention device presses against an outside cortex of the bone tunnel.

Further, the graft insertion step further comprises extending a portion of the soft tissue graft outside the bone tunnel and the retention device insertion step further comprises pressing the extended portion of soft tissue graft between the outside cortex of the bone tunnel and the anchoring device. The method can also include coupling the tendon or ligament to the anchoring device and wherein the coupling step is performed by suturing the tendon or ligament to the anchoring device. Additionally, the method can include placing the anchoring device within the tunnel such that it lays substantially flush with the outside cortex of the bone tunnel. In such an arrangement, the method causes spikes to embed in the outside cortex of the bone tunnel.

BRIEF DESCRIPTION OF THE DRAWINGS

The foregoing and other objects and features of the present invention will become more fully apparent from the following description and appended claims, taken in conjunction with the accompanying drawings. Understanding that these drawings depict only typical embodiments of the invention and are, therefore, not to be considered limiting of its scope, the invention will be described with additional specificity and detail through use of accompanying drawings in which:

DESCRIPTION OF SPECIFIC EMBODIMENTS OF THE INVENTION

It will be readily understood that the components of the present invention, as generally described and illustrated in the Figures herein, could be arranged and designed in a wide variety of different configurations. Thus, the following more detailed description of the preferred embodiments of the endosteal anchoring device and method of the present invention, as represented in FIGS. 1 through 8, is not intended to limit the scope of the invention, as claimed, but it is merely representative of the presently preferred embodiments of the invention.

The specific embodiments of the invention will be best understood by reference to the drawings, wherein like parts are designated by like numerals throughout. When reconstructing or replacing a torn or dislocated ligament, care should be taken to provide a means for connecting a ligament to its predetermined connection site and maintaining it firmly thereto. Generally, surgical procedures involve either the use of natural biological tissue grafts or prosthetic ligaments, simulated to mimic the parameters of strength, flexibility and positioning of the natural ligament it replaces.

Figure 1:
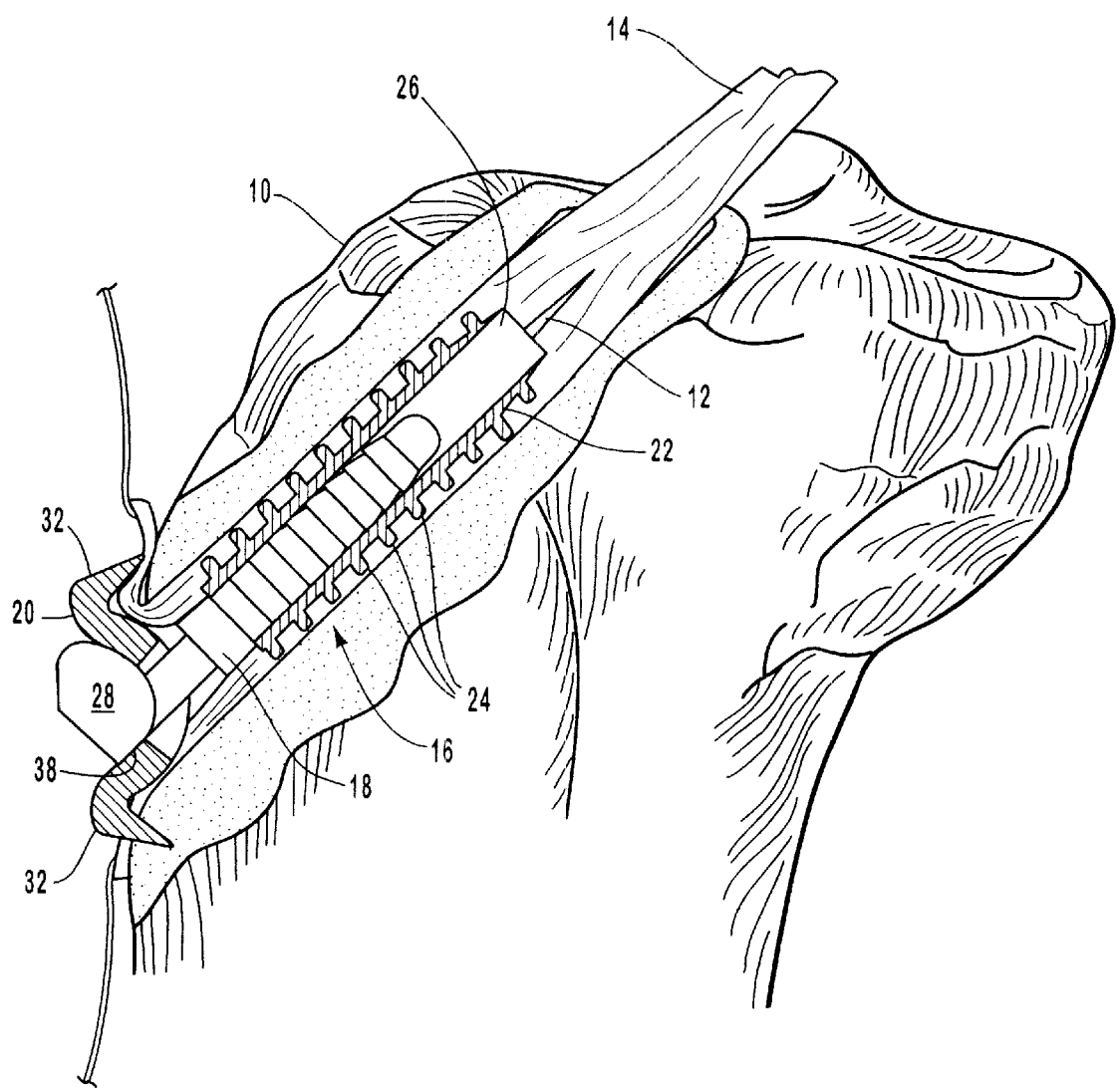
FIG. 1 is a perspective view illustrating one embodiment of the endosteal anchoring device of the present invention.

As shown in FIG. 1, to accommodate a ligament graft to a fixation site, the present invention offers a device for urging a ligament 14 against the peripheral surface of a tunnel 12 formed within a bone 10, by implementing an endoscopic technique designed primarily for use with arthroscopic assistance. When reconstructing or replacing a torn or dislocated ligament, particularly the anterior cruciate ligament (ACL) of the knee, a bone tunnel 12 is generally formed in the femur and/or tibia for positioning the natural or synthetic ligament graft 14 therein. Tunnel 12 extends from a first opening to a second opening on the opposite side of bone 10.

One specific method provided by the present invention for replacing or reconstructing dislocated ligaments utilizes an endosteal anchoring member 16, formed of plastic, bone, stainless steel or any other suitable material. The endosteal anchoring member 16 consists of a retention device 18, an anchoring or holding device 20, and a rigid securing body 22. Securing body 22, also shown in detail alone in FIG. 3, has ridges or screw threads 24 about its outer circumference and an opening 26, which extends nearly to the opposite end of body 22. The endosteal anchoring device is manufactured from a material suitable for sterilization and human implantation, and comprised of either a permanent non-biodegradable material or a biodegradable material capable of being absorbed by the body while maintaining the essential rigid qualities required to accommodate its anchoring functions. Further, these materials can be impregnated or coated with healing enhancing substances, such as Bone Morphogenic Protein (BMP) or Calcium Phosphate (CaPo4).

Figure 4A:
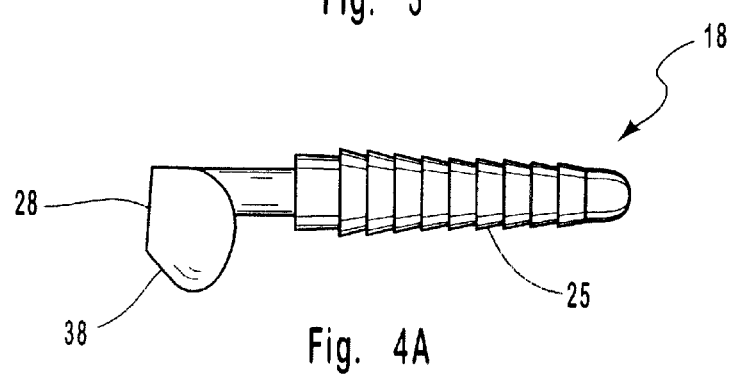
FIG. 4A is a side view of the retention device as shown in FIG. 1 in accordance with the present invention.
Figure 4B:
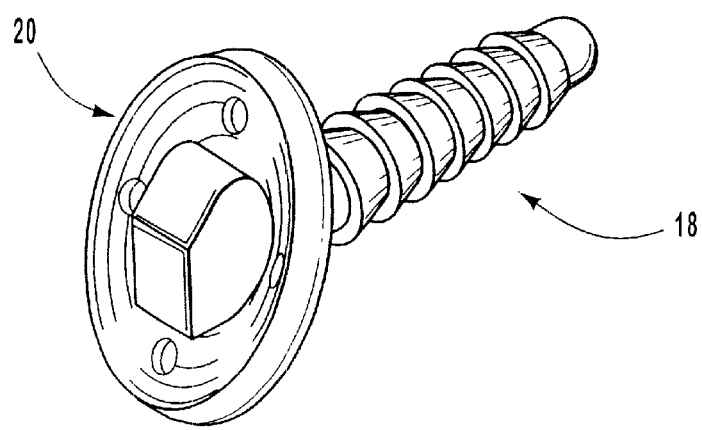
FIG. 4B is a side view of the retention device as shown in FIG. 1 in accordance with the present invention.

In this embodiment, the ligament graft 14 extends through tunnel 12 to the outer surface of bone 10. Thread or string can be used to attach to one end of ligament 14 to draw it into tunnel 12. Other methods of inserting ligament 14 within tunnel 12 are readily apparent to those skilled in the art. The graft 14 then is pressed against the outer surface to graft with bone 10 for recovery and to anchor the graft physically for long-term support. It is intended that ligament graft 14 is held in place against the outer bone surface by anchoring member 16. To accomplish this, anchoring member 16 utilizes retention device 18 and anchoring device 20. Retention device 18, which is also shown in greater detail in FIG. 4A, fits within opening 26 of securing body 22 after body 22 is placed within tunnel 12. Retention device 18 also has ridges or screws 25 on its outer surface to engage with the interior of securing body 22 in a fixed arrangement, as shown in FIG. 4B. Retention device 18 further includes a retaining or retention head 28, which is designed to be larger than the diameter of the length of securing body 22. Retention device 18 mates to a holding or anchoring device 20, which has a given width sufficient that tunnel 12 can be wide enough to accept retention device 18 and securing body 22 and that is narrow enough to prevent anchoring device 20 from passing though the tunnel.

Figure 5:
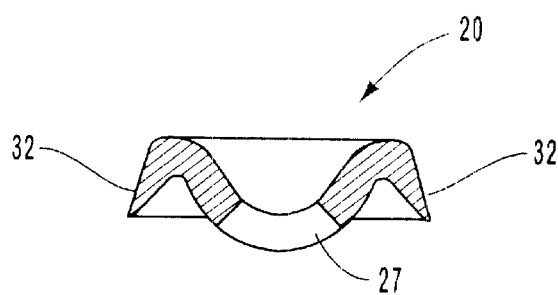
FIG. 5 is a cut-away side view of the anchoring device as shown in FIG. 1 in accordance with the present invention.

Anchoring device 20, which is also shown in greater detail in FIG. 5, has an opening 27 and is generally washer-shaped. Along its outer perimeter is an outer lip or plurality of generally outwardly and downwardly projecting spikes 32 that are utilized to engage the bone surface of bone 10 during the re-attachment procedure. Each spike 32 penetrates ligament 14 as well as bone 10 to secure ligament 14 to the surface of bone 10. Anchoring device 20 further includes a plurality of openings 32 through which sutures may pass to secure the ligament within the tunnel without requiring the ligament to extend outside the tunnel, which is shown in detail in FIG. 2.

Retention device 18 and securing body 22 may be formed either of plastic, bone, stainless steel or any other suitable material, but not necessarily the same material, and both comprise a substantially elongated body. The endosteal anchoring device 16 is manufactured from a material suitable for sterilization and human implantation, and comprised of either a permanent non-biodegradable material or a biodegradable material capable of being absorbed by the body while maintaining the essential rigid qualities required to accommodate its anchoring functions.

Alternatively, through tunnel 12 within bone 10 can be wide enough that securing body 22 does not actually apply any pressure to ligaments 14 to hold them against the interior surface of the bone. Rather, securing body 22 holds anchoring device in the same position ligaments 14 without being pressure fitted within tunnel 12.

Figure 2:
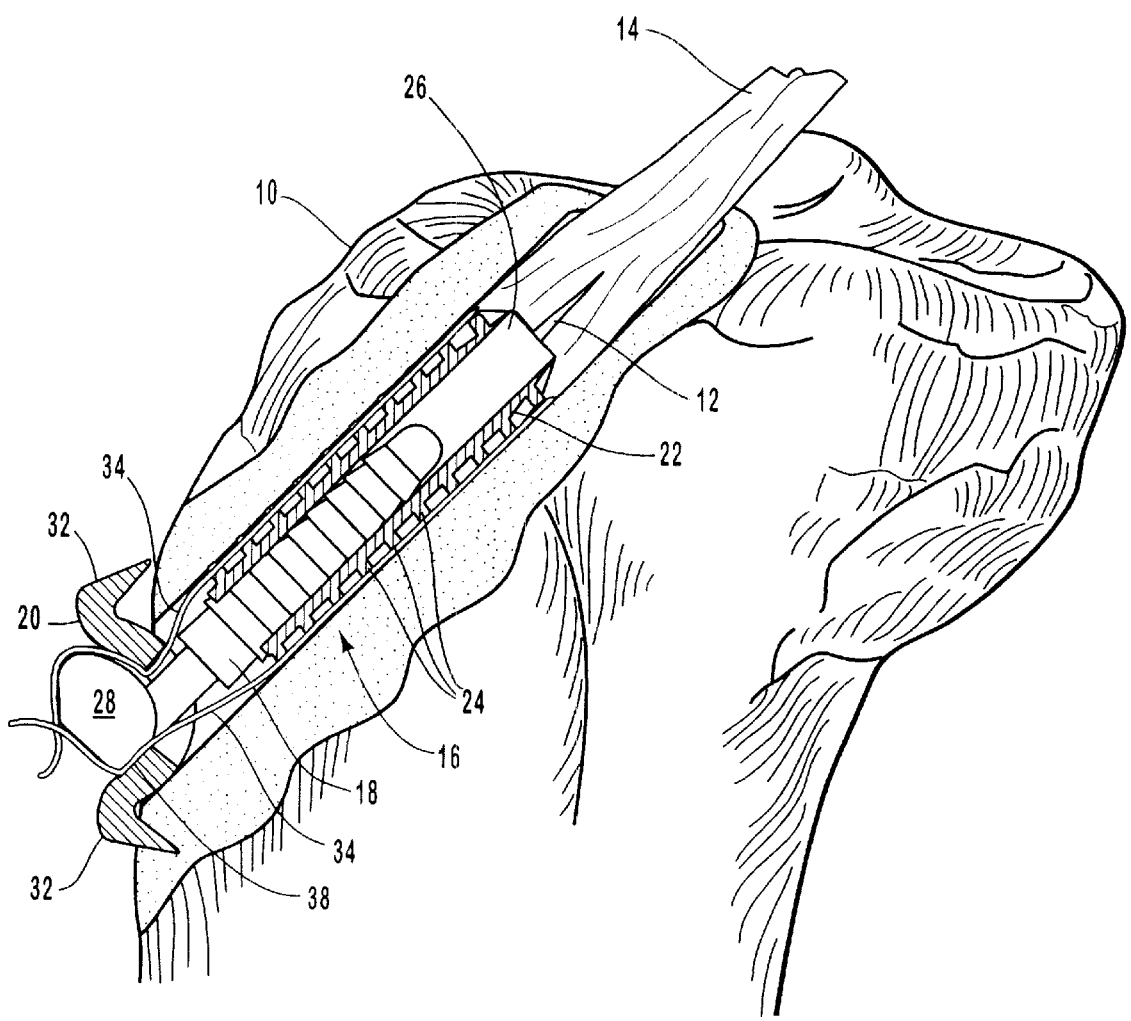
FIG. 2 is a perspective view illustrating a second implementation of the endosteal anchoring device of the present invention.

FIG. 2 illustrates the same perspective cross-sectional view of a re-attachment procedure involving the anchoring device of the present invention as shown in FIG. 1. In this embodiment, several lengths of surgical thread or sutures 34 are connected to the ligament 14 and looped through openings 36 in anchoring device 30. Ligament 14 is retained within tunnel 12 because anchoring device 30 engages the bone surface. Since the support is on the outer bone surface, rather than against the interior bone surface, a stronger connection and graft are made due the to the stronger structure of the bone exterior over the bone interior. Spikes 32 engage the bone surface to provide fixed support of the anchoring system 14. The interior edge of each of openings 36 is rounded or coated so as to have a relatively smooth or dull surface to prevent the openings from cutting through sutures 34.

The retention head 28 of retention device 18 is not only generally rounded, but also includes a substantially flat surface 38 generally parallel with the length of device 18. Flat surface 38 provides for a locking fit between head 28 and anchoring device 20. Initially, anchoring device 20 floats in order to provide a self-aligning attachment to the bone surface. Next, once a suitable attachment angle has been found, the flat surface 38 locks with an inner surface along a cupped portion of anchoring device 20. This arrangement holds anchoring device 20 in place until spikes 32 penetrate the bone surface for fixed support.

Figure 3:
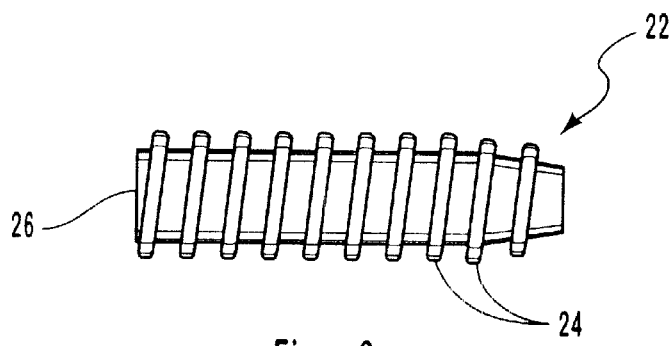
FIG. 3 is a side view of the securing device as shown in FIG. 1 in accordance with the present invention.

FIG. 3 illustrates a side plan view of securing body 22 with its screw ridges or screw threads 24 and opening 26. Retention device 18 inserts within opening 26 with ridges 25 engaging the inner wall of body 22 to provide a friction or pressure fit therein.

Figure 6:
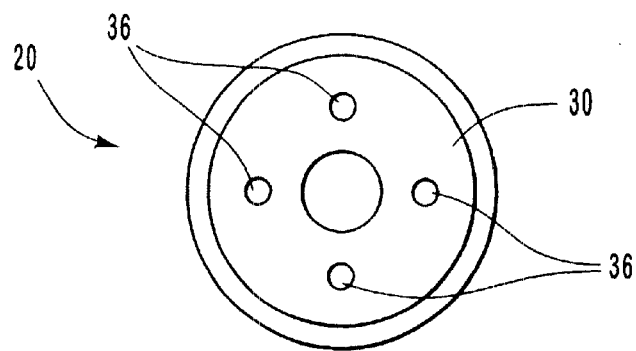
FIG. 6 is a top plan view of the anchoring device as shown in FIG. 5 in accordance with the present invention.

An alternative anchoring device 120 is shown in FIG. 6. Anchoring device 120 is generally tapered or conical-shaped and has an opening 130 extending through the body of the device from the top to the base, where a plurality of spikes 132 are formed. The taper or conical shape of device 120 acts as a seat that engages the tunnel opening of the bone so that anchor 120 lodges within the bone opening without passing therethrough. Anchor 120 further includes a plurality of ridges 134 that provide additional friction or pressure fitting to the bone surface.

Figure 7:
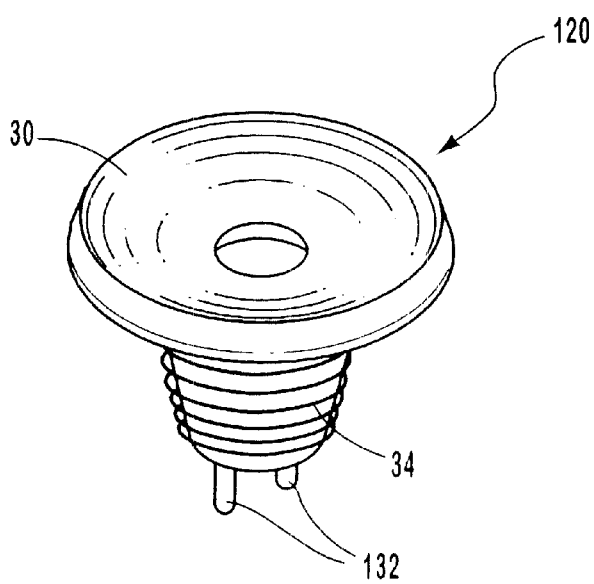
FIG. 7 is perspective view illustrating a second embodiment of the anchoring device in accordance with the present invention.

FIG. 7 illustrates a top plan view of either anchor device 20 or anchor 120 as shown in FIG. 6. The anchor includes opening 30, as well as a plurality of retention or suture openings 32 about the perimeter of opening 30. Suture openings 36 allow for threads or other suitable suture type material to be threaded through openings 36 and attached to the ligament to be grafted into the bone structure as shown in either FIG. 1 or FIG. 2.

Figure 8:
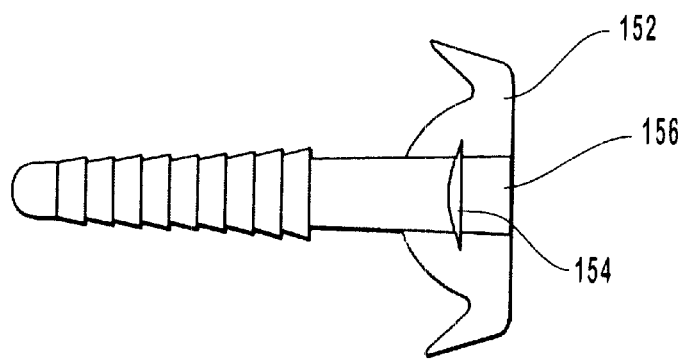
FIG. 8 illustrates a side view of a third embodiment of the anchoring device in accordance with the present invention.

FIG. 8 illustrates yet another alternative view of the anchoring assembly. Rather than have discrete elements of the retention device 18 and anchoring device 20, they may be integrated into a single retention and anchoring device 150, wherein an anchoring device 152 is pivotally pinned 154 to a head portion 156 of device 150. Suture openings 158 can be placed within head portion 156 or in anchoring device 152 for securing a ligament to device 150, rather than with the spikes 160 on the outer perimeter of head portion 156. Device 150 then inserts into securing device 22 within tunnel 12 like that shown in either FIG. 1 or 2. Another embodiment can include having the anchoring device mate to the head portion in ball and socket joint, which allows pivoting of the anchoring portion for self alignment and seating into the cortex of the bone.

While specific embodiments of the endosteal anchoring device have been shown and described herein, the present invention may be embodied in other specific forms without departing from its spirit or essential characteristics. The described embodiments are to be considered in all respects only as illustrative, and not restrictive. The scope of the invention is, therefore, indicated by the appended claims, rather than by the foregoing description. All changes which come within the meaning and range of equivalency of the claims are to be embraced within their scope.

What is claimed is:

1. An anchoring apparatus that secures a tendon or ligament within an interior opening of a bone structure, the anchoring apparatus comprising:

a securing device having an elongated body with an outer surface and an inner channel, wherein the tendon or ligament is secured between a bone wall of the open bone structure and the outer surface of the securing device, and wherein the securing device is configured for placement completely within the open bone structure;

a retention device having an elongated body and a retention head, wherein at least a portion of the elongated body extends down the inner channel of the securing device to cause a bias on the tendon or ligament in a direction toward the bone wall, wherein the retention head includes a rounded portion and a flat portion, and wherein the flat portion is parallel to the length of the elongated body; and a holding device that is connected to the retention head and extends outside of an outer surface of the bone structure wherein at least a portion of the holding device is configured to lock with the flat portion of the retention head, and wherein another portion of the holding device provides a bias in a direction that is transverse to the bias caused by the elongated body extending down the inner channel of the securing device.

2. The anchoring apparatus according to claim 1, wherein the holding device comprises a washer that includes at least one retention spike to engage the bone structure and an opening configured to receive the elongated body of the retention device therethrough, but not the retention head.

3. The anchoring apparatus according to claim 2, wherein the rounded portion of the retention head provides a pivotal connection with the holding device.

4. The anchoring apparatus according to claim 1, wherein the securing device includes threads on the outer surface.

5. The anchoring apparatus according to claim 1, wherein the holding device includes a plurality of apertures that retain means for securing the tendon or ligament to the anchoring apparatus.

6. An anchoring apparatus that secures a tendon or ligament within an interior opening of a bone structure, comprising:

a securing device having an elongated body with an outer surface and an inner channel, wherein the tendon or ligament is secured against a bone wall of the open bone structure and the outer surface of the securing device and wherein the securing device is configured to be located completely within a channel created in the open bone structure;

a retaining device having an elongated body and a retention head, wherein at least a portion of the elongated body extends down the inner channel of the securing device to cause a bias on the tendon or ligament in a direction toward the bone wall, wherein the retention head includes a rounded portion and a flat portion, and wherein the flat portion is parallel to the length of the retaining device; and an anchoring device that is connected to the retention head of the retaining device and is located outside of the channel of the open bone structure such that a portion of the tendon or ligament extends outside the channel of the open bone structure and is held in place against an outer surface of the open bone structure by the anchoring device providing a bias in a direction that is transverse to the bias caused by the elongated body extending down the inner channel of the securing device, wherein at least a portion of the anchoring device is configured to lock with the flat portion of the retention head, and wherein the orientation of the elongated body is allowed to be transverse in relation to the anchoring device.

7. The anchoring apparatus according to claim 6, wherein the anchoring device comprises a washer that includes at least one anchoring spike to engage the bone structure and an opening configured to receive the elongated body of the retention device therethrough, but not the retention head.

8. The anchoring apparatus according to claim 7, wherein the rounded portion of the retention head provides a pivotal connection with the holding device.

9. The anchoring apparatus according to claim 6, wherein the securing device includes threads on the outer surface.

10. The anchoring apparatus according to claim 6, wherein the anchoring device includes a plurality of apertures that retain means for securing the tendon or ligament to the anchoring apparatus.

\* \* \* \* \*